US011295851B2

(12) United States Patent
Marchal

(10) Patent No.: US 11,295,851 B2
(45) Date of Patent: Apr. 5, 2022

(54) DEVICES AND METHODS OF OPTIMAL PERSONALIZED DAILY HYDRATION

(71) Applicant: NESTEC S.A., Vevey (CH)

(72) Inventor: Eric Marchal, Vittel (FR)

(73) Assignee: Societe des Produits Nestle S.A., Vevey (CH)

( * ) Notice: Subject to any disclaimer, the term of this patent is extended or adjusted under 35 U.S.C. 154(b) by 357 days.

(21) Appl. No.: 16/461,911

(22) PCT Filed: Nov. 27, 2017

(86) PCT No.: PCT/EP2017/080457
§ 371 (c)(1),
(2) Date: May 17, 2019

(87) PCT Pub. No.: WO2018/099839
PCT Pub. Date: Jun. 7, 2018

(65) Prior Publication Data
US 2019/0279758 A1    Sep. 12, 2019

Related U.S. Application Data

(60) Provisional application No. 62/429,431, filed on Dec. 2, 2016.

(51) Int. Cl.
*G16H 20/60* (2018.01)
(52) U.S. Cl.
CPC .................................. *G16H 20/60* (2018.01)
(58) Field of Classification Search
CPC ....................................................... G16H 20/60
See application file for complete search history.

(56) References Cited

U.S. PATENT DOCUMENTS

| 7,493,232 B1 | 2/2009 | Surina |
| 2005/0043595 A1 | 2/2005 | Miller |

(Continued)

FOREIGN PATENT DOCUMENTS

| WO | 2013123418 | 8/2013 |
| WO | 2016122804 | 8/2016 |

OTHER PUBLICATIONS

Kenefick et al. "Dehydration and Rehydration" 2012, retrieved from the Internet at http://www.dtic.mil/dtic/tr/fulltext/u2/a559016.pdf, XP055456260, 16 pages (Year: 2012).*

(Continued)

*Primary Examiner* — Jennifer N Welch
*Assistant Examiner* — Parmanand D Patel
(74) *Attorney, Agent, or Firm* — K&L Gates LLP

(57) ABSTRACT

Devices and methods analyze daily hydration in an individual. An application can confirm if typical daily water intake by an individual participating is sufficient to maintain hydration and/or can determine an optimal personalized hydration plan to maintain or improve hydration for the individual. The application can estimate water losses during each of a plurality of activities by considering one or more characteristics of the individual, such as weight, height, gender, heart rate at rest, maximal heart rate, $VO_2$ max, effort intensity, and type of clothes worn, and/or one or more characteristics of each of the plurality of activities, such as the specific category of activity, the time duration, and the location of each of the plurality of activities (e.g., ambient temperature and moisture). The daily hydration plan can improve daily performance by the individual, for example one or more of decreased fatigue, increased motivation, improved mood, or better cognitive functioning.

13 Claims, 5 Drawing Sheets

(56) References Cited

U.S. PATENT DOCUMENTS

| | | | | |
|---|---|---|---|---|
| 2006/0275431 | A1* | 12/2006 | Bagley | A61K 33/00 424/600 |
| 2009/0063090 | A1* | 3/2009 | Surina | G01K 13/20 702/160 |
| 2013/0158368 | A1* | 6/2013 | Pacione | A61B 5/318 600/301 |
| 2014/0221792 | A1 | 8/2014 | Miller et al. | |
| 2014/0335490 | A1* | 11/2014 | Baarman | G16H 20/30 434/236 |
| 2015/0196251 | A1 | 7/2015 | Outwater et al. | |
| 2016/0022209 | A1* | 1/2016 | Fraisl | A61B 5/7282 600/590 |

OTHER PUBLICATIONS

Sawka "Chapter 4—Water" 2005, retrieved from the Internet at http://www.dtic.mil/dtic/tr/fulltext/u2/a433916.pdf, XP055456190, pp. 73-185 (Year: 2005).*

Shapiro et al. "Predicting Sweat Loss Response to Exercise, Environment and Clothing" European Journal of Applied Physiology, 1982, vol. 48, pp. 83-96.

Kenefick et al. "Dehydration and Rehydration" 2012, retrieved from the Internet at http://www.dtic.mil/dtic/tr/fulltext/u2/a559016.pdf, XP055456260, 16 pages.

Sawka "Chapter 4—Water" 2005, retrieved from the Internet at http://www.dtic.mil/dtic/tr/fulltext/u2/a433916.pdf, XP055456190, pp. 73-185.

\* cited by examiner

| | |
|---|---|
| How much fruits and vegetables do you consume per day ? (number of serving) = | n1 |
| How much meat/fish do you consume per day ? (number of serving) = | n2 |
| How much pasta, rice, potatoes do you consume per day ? (number of serving) = | n3 |
| How much mixed dishes (pizza, paella, couscous, moussaka ,,,) do you consume per day ? (number of serving) = | n4 |
| How much cheese do you consume per day ? (number of serving) = | n5 |
| How much dairy products do you consume per day ? (number of serving) = | n6 |
| How much pastry or dessert do you consume per day ? (number of serving) = | n7 |
| How much bread do you consume per day ? (number of serving) = | n8 |
| How much fluid (water, juice, coffee, tea, milk ...) do you consume per day ? (1 glass = 0,20 L) = | n9 |

$$m_{diet} = (n1 * 0.085) + (n2 * 0.06) + (n3 * 0.075) + (n4 * 0.065) + (n5 * 0.015) + (n6 * 0.105) + (n7 * 0.075) + (n8 * 0.0105) + (n9 * 0.2)$$

FIG. 5

DEVICES AND METHODS OF OPTIMAL PERSONALIZED DAILY HYDRATION

CROSS REFERENCE TO RELATED APPLICATIONS

The present application is a National Stage of International Application No. PCT/EP2017/080457, filed on Nov. 27, 2017, which claims priority to U.S. Provisional Patent Application No. 62/429,431, filed on Dec. 2, 2016, the entire contents of which are being incorporated herein by reference.

BACKGROUND

The present disclosure generally relates to devices and methods for analyzing daily hydration in an individual. More specifically, the present disclosure relates to an application that can determine an optimal personalized daily hydration plan for an individual based at least partially on the plurality of activities in the day.

Individuals typically lose 0.4 to 0.5 liters of water per day just from breathing, which is additional to water losses from various activities performed throughout the day. Individuals typically drink when they are thirsty and not to prevent dehydration. However, by the time an individual is thirsty, they are already in the initial stages of dehydration. Thirst is not a good indicator of whether or not an individual should drink and how much to drink. Moreover, even if an individual is drinking with the intent to stay hydrated, they usually do not know how much to drink in order to maintain hydration.

SUMMARY

The present disclosure relates to an application that can confirm if typical water intake by an individual is sufficient to maintain hydration through their daily activities and/or can determine an optimal personalized daily hydration plan to maintain or improve hydration for an individual. More specifically, the application can estimate water gain and water losses during each of a plurality of daily activities, such as one or more of sleep, work/labor, meals, sitting activities, or a sports training session or match, by considering one or more characteristics of the individual, such as weight, height, gender, heart rate at rest, maximal heart rate, VO₂ max, and type of clothes worn. Improved hydration can achieve a corresponding improvement in daily performance, for example one or more of decreased fatigue, increased motivation, improved mood, or better cognitive functioning.

Accordingly, in a general embodiment, the present disclosure provides a method of decreasing or preventing dehydration from a plurality of activities of an individual. The method comprises: accepting user input into an application provided by a device comprising a processor, the user input comprising information identifying one or more characteristics of each of the plurality of activities and identifying one or more characteristics of the individual; analyzing the information provided by the user input to determine a total water loss by the individual from the plurality of activities, and the analyzing is performed by the device providing the application; and displaying on the device a personalized hydration plan that comprises a total amount of water intake for the plurality of activities, and the personalized hydration plan is based at least partially on the total water loss determined from the information.

In an embodiment, a total time duration of the plurality of activities is approximately twenty-four hours, and the personalized hydration plan is a daily hydration plan.

In an embodiment, the analyzing of the information for a first activity is performed using at least one variable or equation different than the analyzing of the information for a second activity different than the first activity even if the information is otherwise identical.

In an embodiment, the information provided by the user input identifies food products consumed during the plurality of activities, the method comprises determining a total amount of water intake from the food products, and the analyzing of the information to determine the total water loss is based at least partially on the total amount of water intake from the food products. The information can identify a category of each of the food products and a number of servings of the category of the food products consumed by the individual, and the total amount of water intake from the food products can be based at least partially on the category of each of the food products and the number of servings of the category of the food products.

In an embodiment, the information entered by the user input identifies a specific category of activity for each of the plurality of activities; the method comprises determining a caloric expenditure for each of the plurality of activities based at least partially on the specific categories of activity, a time duration thereof, and an age, gender and weight of the individual. The method can comprise determining a total caloric expenditure for the plurality of activities. The personalized hydration plan can be based at least partially on the total caloric expenditure for the plurality of activities.

In an embodiment, at least one of the one or more characteristics of the individual is selected from the group consisting of weight, height, gender, heart rate at rest, maximal heart rate, VO₂ max, a type of clothes worn during one or more of the plurality of activities, and combinations thereof.

In an embodiment, the analyzing of the information to determine the total water loss comprises determining water loss in sweat by the individual in each of the plurality of activities. The information entered by the user input can comprise data identifying a specific category of activity for each of the plurality of activities, a time duration of each of the plurality of activities, weight and/or height of the individual, age of the individual, and gender of the individual. The determining of the water loss in sweat by the individual in each of the plurality of activities can be based at least partially on the data.

In an embodiment, the analyzing of the information to determine the total water loss by the individual comprises determining water loss in urine by the individual in each of the plurality of activities, and the personalized hydration plan is based at least partially on the water loss in urine by the individual in each of the plurality of activities. The information entered by the user input can comprise data identifying a specific category of activity for each of the plurality of activities, a time duration of each of the plurality of activities, heart rate at rest of the individual, age and/or gender of the individual, and optionally VO₂ max of the individual. The determining of the water loss in urine by the individual can be based at least partially on the data.

In an embodiment, the analyzing of the information to determine the total water loss by the individual comprises determining respiratory water loss by the individual in each of the plurality of activities, and the personalized hydration plan is based at least partially on the respiratory water loss by the individual in each of the plurality of activities. The information entered by the user input can comprise data identifying a specific category of activity for each of the plurality of activities, a time duration of each of the plurality of activities, weight of the individual, height of the individual, age of the individual, gender of the individual, and ambient temperature. The determining of the respiratory water loss by the individual can be based at least partially on the data.

In an embodiment, the analyzing of the information to determine the total water loss by the individual comprises determining insensible water loss by the individual in each of the plurality of activities, and the personalized hydration plan is based at least partially on the insensible water loss. The information entered by the user input can comprise data identifying a specific category of activity for each of the plurality of activities, a time duration of each of the plurality of activities, weight of the individual, and height of the individual. The determining of the insensible water loss can be based at least partially on the data and preferably at least partially on the ambient temperature and/or humidity.

In an embodiment, the analyzing of the information to determine the total water loss by the individual comprises determining an amount of endogenic water formed by the individual in each of the plurality of activities, and the total water loss by the individual from the plurality of activities is based at least partially on the endogenic water formed by the individual in each of the plurality of activities. The information entered by the user input can comprise data identifying a specific category of activity for each of the plurality of activities, a time duration of the specific category of activity of each of the plurality of activities, weight of the individual, age of the individual, and gender of the individual. The determining of the amount of endogenic water formed by the individual in each of the plurality of activities can be based at least partially on the data.

In an embodiment, the accepting of the user input comprising the information into the application and the analyzing of the information are completed before the individual participates in the plurality of activities.

In an embodiment, the total water loss from the plurality of activities is determined by adding (i) a total water loss from sweat and/or a total insensible water loss from the plurality of activities, (ii) water loss from urine from the plurality of activities and (iii) respiratory water loss from the plurality of activities, and subtracting (iv) endogenic water from the plurality of activities and (v) water intake from food products consumed during the plurality of activities.

In an embodiment, the personalized daily hydration plan improves daily performance in the individual during the plurality of activities, the improved daily performance comprises one or more of decreased fatigue, increased motivation, improved mood, or better cognitive functioning.

In another embodiment, the present disclosure provides a method of decreasing or preventing dehydration from a plurality of activities of an individual. The method comprises: accepting user input into an application provided by a device comprising a processor, the user input identifying a usual amount of water intake by the individual during the plurality of activities, identifying information identifying one or more characteristics of each of the plurality of activities, and identifying one or more characteristics of the individual; analyzing the user input to determine a total water loss by the individual from the plurality of activities, and the analyzing is performed by the device providing the application; and displaying an output on the device, the application is configured to display a first output that is a confirmation that the usual amount of water intake by the individual during the plurality of activities is sufficient to prevent dehydration from the plurality of activities, the application is configured to display a second output comprising a personalized hydration plan that identifies a daily amount of water intake, and the personalized hydration plan is based at least partially on the total water loss determined from the information, wherein the output displayed by the application is the first output when the total water loss from the usual amount of water intake by the individual during the plurality of activities is less than a threshold, and the output displayed by the application is the second output when the total water loss from the usual amount of water intake by the individual during the plurality of activities is more than the threshold.

In yet another embodiment, the present disclosure provides a method of decreasing or preventing dehydration from a plurality of activities of an individual. The method comprises: entering user input into an application provided by a device comprising a processor, the user input comprising information identifying a usual amount of water intake by the individual during the plurality of activities, identifying information identifying one or more characteristics of each of the plurality of activities, and identifying one or more characteristics of the individual; and administering water to the individual according to a personalized hydration plan displayed in the application by the device. The personalized hydration plan can comprise an amount of water intake for the plurality of activities, and the personalized hydration plan can be based at least partially on a total water loss by the individual from the plurality of activities which is based at least partially on the information in the user input.

In yet another embodiment, the present disclosure provides a device comprising a processor configured to accept user input into an application provided by the device. The user input comprises information identifying one or more characteristics of each of a plurality of activities of an individual and identifying one or more characteristics of the individual. The processor is further configured to analyze the user input to determine a total water loss by the individual from the plurality of activities. The processor is further configured to display on the device a personalized hydration plan comprising an amount of water intake for the plurality of activities of the individual, and the personalized hydration plan is based at least partially on the total water loss by the individual from the plurality of activities.

An advantage of the present disclosure is to create an optimal personalized daily hydration plan for an individual.

Another advantage of one or more embodiments provided by the present disclosure is to maintain or improve daily hydration.

Still another advantage of one or more embodiments provided by the present disclosure is to guide an individual participating in daily activities to use water intake directed to hydration, not merely thirst.

Yet another advantage of one or more embodiments provided by the present disclosure is to consider hydration factors not typically addressed for an individual participating in daily activities.

Furthermore, another advantage of one or more embodiments provided by the present disclosure is to mitigate or prevent decreased performance that results from dehydration in an individual participating in daily activities, for example mitigating or preventing one or more of fatigue, decreased motivation, negative mood, or reduced cognitive functioning.

An additional advantage of one or more embodiments provided by the present disclosure is to identify a volume of water intake for an individual participating in daily activities.

Another advantage of one or more embodiments provided by the present disclosure is to predict water loss for an individual participating in daily activities.

Still another advantage of one or more embodiments provided by the present disclosure is to prevent or minimize water loss in an individual participating in daily activities.

Yet another advantage of one or more embodiments provided by the present disclosure is to consider various types of water loss experienced by an individual participating in daily activities.

Furthermore, another advantage of one or more embodiments provided by the present disclosure is an easily navigable interactive tool to create an optimal personalized daily hydration plan for an individual.

An additional advantage of one or more embodiments provided by the present disclosure is to use urine loss, respiratory water loss, and at least one of insensible water loss and sweat loss to determine water need for an individual participating in daily activities.

Another advantage of one or more embodiments provided by the present disclosure is to use the type of clothing worn by an individual participating in daily activities to determine water need.

Still another advantage of one or more embodiments provided by the present disclosure is to use endogenic water and water intake from food and drink during the day to determine water need for an individual participating in daily activities.

Yet another advantage of one or more embodiments provided by the present disclosure is an interactive tool accessible over the internet that requests information from an individual participating in daily activities and then uses the information to create a personalized optimal daily hydration plan for the individual.

Furthermore, another advantage of one or more embodiments provided by the present disclosure is to confirm if the typical hydration by an individual participating in daily activities is sufficient to maintain hydration.

An additional advantage of one or more embodiments provided by the present disclosure is to determine the caloric expenditure of each of the activities that make up a day.

Yet another advantage of one or more embodiments provided by the present disclosure is an optimal personalized daily hydration plan that considers mineral loss in an individual participating in daily activities and addresses these deficits.

Additional features and advantages are described in, and will be apparent from, the following Detailed Description and the Figures.

BRIEF DESCRIPTION OF DRAWINGS

FIG. 5 shows user input identifying food products consumed during a plurality of activities and the determination of water intake from the food products ($m_{diet}$) in liters in one or more embodiments of the methods provided by the present disclosure.

DETAILED DESCRIPTION

Definitions

Figure 1:
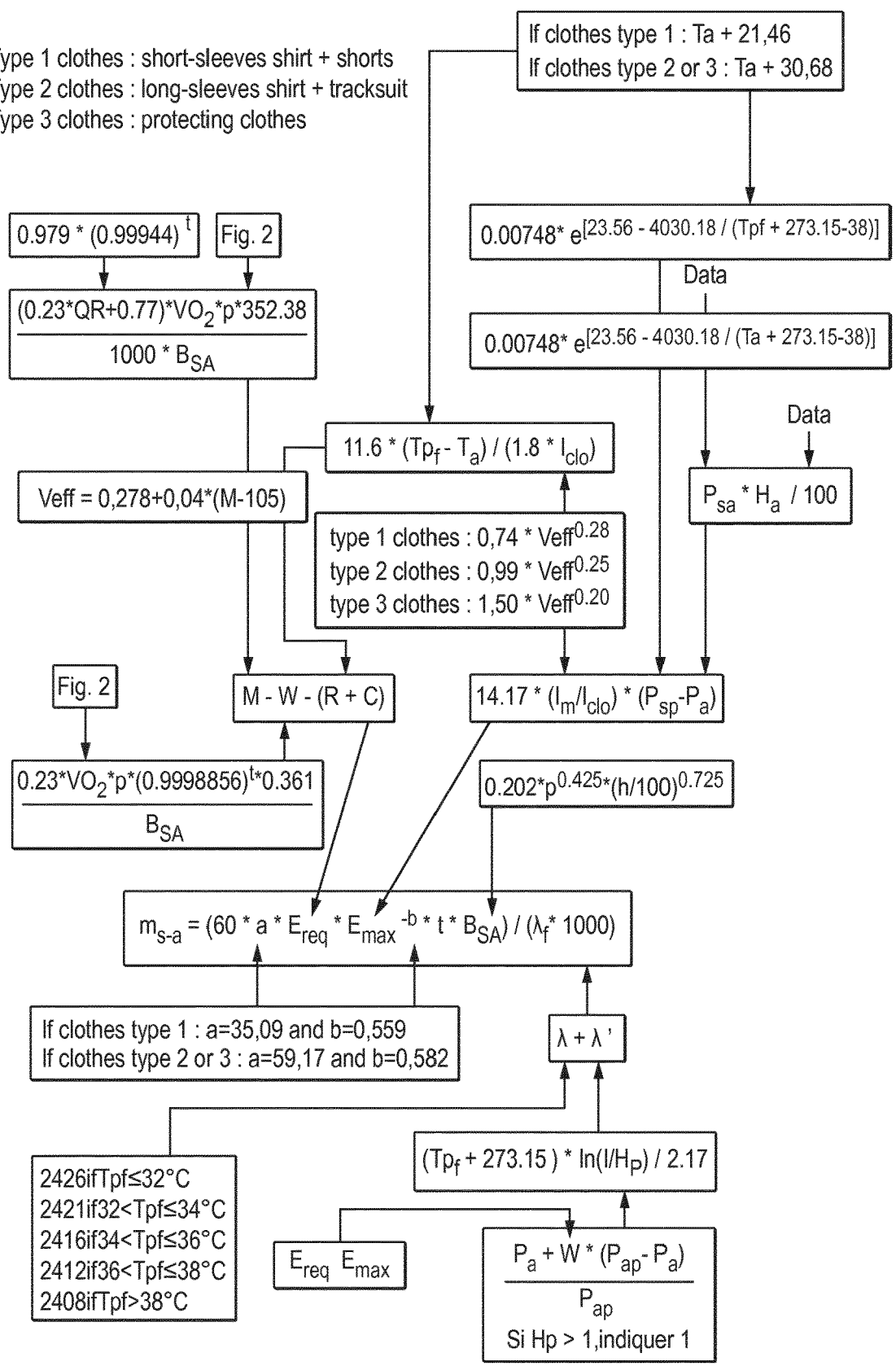
FIG. 1 shows determination of the volume of sweat loss from each of a plurality of activities ($m_{s-a}$) in liters in one or more embodiments of the methods provided by the present disclosure.

Some definitions are provided hereafter. Nevertheless, definitions may be located in the "Embodiments" section below, and the above header "Definitions" does not mean that such disclosures in the "Embodiments" section are not definitions.

All percentages and ratios are by weight unless otherwise specified. As used herein, "about" and "approximately" are understood to refer to numbers in a range of numerals, for example the range of −10% to +10% of the referenced number, preferably within −5% to +5% of the referenced number, more preferably within −1% to +1% of the referenced number, most preferably within −0.1% to +0.1% of the referenced number. A range that is "between" two values includes those two values.

The relative term "preventing dehydration" includes reduction of risk and/or severity of dehydration. The relative term "decreasing dehydration" means that the hydration of the individual at the end of a day in which the individual utilizes the personalized daily hydration plan disclosed herein (e.g., consumes the amount of water identified by the plan) is greater than the hydration of the individual at the end of a day in which the individual consumes their usual amount of water (e.g., without using the personalized daily hydration plan).

Similarly, the relative term "improving daily performance" means that one or more of fatigue, motivation, mood, or cognitive functioning is better during a day in which the individual utilizes the personalized daily hydration plan disclosed herein (e.g., consumes the amount of water identified by the plan) relative to a day in which the individual consumes their usual amount of water (e.g., without using the personalized daily hydration plan).

The term "administering" includes both an individual administering the referenced composition to themselves and another individual administering the referenced composition to the individual.

An "activity" is any portion of the day in which the actions of an individual can be characterized, including sleep and sitting. An activity can be a sporting activity (a game/match or training session) or a non-sporting activity. The present disclosure is not limited to a specific activity and includes any activity in which an individual can have water loss or water intake. As used herein, a "daily activity" is not necessarily performed by the individual every day, although some daily activities such as sleeping are indeed typically performed every day. Instead, the term "daily activity" merely requires that the individual performs the activity at least occasionally, i.e., at least one time per week; preferably at least two, three or four times per week; more preferably five or six times per week; most preferably seven times per week.

"Ambient temperature" means the temperature of the immediate surroundings of the activity. In some embodiments, the ambient temperature is the actual measured temperature (e.g., the temperature at the location of the activity). In other embodiments, the ambient temperature is the average temperature of that location in that season, that month, that week, or that day. As used herein, "ambient temperature" does not have its colloquial meaning of the preferred indoor climate-controlled temperature.

The term "database" means the hardware (e.g., a computer) and/or the software (e.g., a computer program such as a computer application) that receives, stores, processes and delivers content that can be accessed, for example, through the internet using a website hosted by the database and/or a web server associated with the database.

The term "automatically" means without user input being necessary. An operation performed "automatically" can comprise one or more actions by the corresponding device, but each of the actions is performed without a requirement of user input.

The terms "provide" and "display" not only include visual representations such as text and/or icons but also include audio representations as well, alone or in combination with visual representations.

The term "data" used herein, and particularly in the figures, is information input by a user of the application.

The terms "food," "food product" and "food composition" mean a product or composition that is intended for ingestion by an individual such as a human and provides at least one nutrient to the individual and/or provides water to the individual. As used herein, these terms include fluids (e.g., beverages).

As used herein and in the appended claims, the singular form of a word includes the plural, and vice versa, unless the context clearly dictates otherwise. Thus, the references "a," "an" and "the" are generally inclusive of the plurals of the respective terms. For example, reference to "a device" or "a method" includes a plurality of such devices or methods.

The term "and/or" used in the context of "X and/or Y" should be interpreted as "X," or "Y," or "X and Y."

The words "comprise," "comprises," and "comprising" are to be interpreted inclusively rather than exclusively. Likewise, the terms "include," "including" and "or" should all be construed to be inclusive, unless such a construction is clearly prohibited from the context. However, the embodiments provided by the present disclosure may lack any element that is not specifically disclosed herein. Thus, a disclosure of an embodiment defined using the term "comprising" also is a disclosure of embodiments "consisting essentially of" and "consisting of" the disclosed components or steps. Where used herein, the term "example," particularly when followed by a listing of terms, is merely exemplary and illustrative, and should not be deemed to be exclusive or comprehensive.

It is noted that the various aspects, features, examples and embodiments of the devices, systems and methods described in the present disclosure may be compatible and/or combined together, unless otherwise specified.

Embodiments

The present inventors developed devices, systems and methods for optimal personalized daily hydration in an individual. For example, a program executed by a device comprising a processor can provide an application that requests information related to one or more characteristics of the individual and/or information related to how a day of the individual is divided into activities (e.g., specific categories of activities and the time duration of each of the specific categories of activities). Then the application can provide an optimal personalized hydration plan for the individual.

The optimal personalized hydration plan can comprise a volume of water intake for the day. The program can estimate water losses during an activity by considering one or more characteristics of the individual, such as weight, height, gender, heart rate at rest, maximal heart rate, $VO_2$ max, effort intensity, and type of clothes worn, and/or one or more characteristics of the activity, such as the specific category of activity, the intensity, the time duration, and the location of the activity (e.g., ambient temperature and/or moisture), as discussed in greater detailed later herein.

In a preferred embodiment, the program considers water intake, water produced by the body, and all types of water loss to determine global water needs for a specific subject daily. For example, the program can determine global water needs daily by adding the amount of water lost from sweat per day to the amount of water lost by urine per day and subtracting endogenic water per day and water intake per day (need=sweat/insensible loss+urine+respiratory steam−endogenic water−water intake). Each of these values can be determined by determining the corresponding amount for each of the plurality of activities into which the day is divided, and then adding the values of the plurality of activities. These determinations allow the program to provide customized advice on water need.

Preferably, the application uses the age and gender of the individual to estimate the $VO_2$ max of the individual. For example, a preferred embodiment of the application estimates the $VO_2$ max as 77.78−(1.15*age) if the individual is a male under the age of 35 years, estimates the $VO_2$ max as 47.65−(0.32*age) if the individual is a male having an age of at least 35 years, estimates the $VO_2$ max as 66.98−(1.07*age) if the individual is a female under the age of 35 years, and estimates the $VO_2$ max as 44.64−(0.3*age) if the individual is a female having an age of at least 35 years.

Water losses can include sweat from each activity ($m_{s-a}$) which occurs when the body becomes unable to evacuate heat only by insensible water losses. FIG. 1 generally illustrates an embodiment of calculations for estimating the volume of sweat loss during an activity ($m_{s-a}$) in liters.

Sweat can be calculated by the following equation derived from Shapiro et al (1982):

$$m_{s-a} = (60 * a * E_{req} * E_{max}^{-b} * t * Bsa)/(\lambda f * 1000)$$

with $E_{req}$=required evaporative cooling ($W \cdot C^{-1} \cdot m^{-2}$), $E_{max}$=maximal evaporative capacity ($W \cdot mmHg^{-1} \cdot m^{-2}$) and $\lambda f$=final vaporization heat ($J \cdot g^{-1}$)

Regarding factors a and b in the sweat equation, these two factors were calculated by Shapiro from 15 groups (111 subjects) doing a basic effort lower than 30% $VO_2$ max in different environments for temperature and clothes. In this case, a=18.7 and b=0.455. To use this formula for intensity of effort higher than 30% $VO_2$ max, which is the usual case for sport effort, the present inventors gathered raw results from twelve papers and used the results therein to calculate a and b for 3 different cases: (i) shorts+T-shirt, (ii) long-sleeve shirt or tracksuit or (iii) protecting clothes. Accordingly, a preferred embodiment estimates water loss from sweat ($m_{s-a}$) using a=35.09 and b=0.559 if clothes type 1 is worn during the activity and estimates water loss from sweat ($m_{s-a}$) using a=59.17 and b=0.582 if clothes type 2 or 3 is worn during the activity. In an embodiment, the data entered by the user to calculate sweat ($m_{s-a}$) comprises length of effort (t), weight, height, gender, and ambient temperature. $E_{req}$, $E_{max}$ and $\lambda f$ are calculated from equations of the literature.

Water losses can include insensible water loss from each activity ($m_{persp-a}$), also known as perspiration, which can occur instead of sweat when activity intensity is low and environmental factors are temperate (ambient temperature, moisture). Insensible water loss includes water that passes through the skin and is lost by evaporation and also includes evaporative water loss from the respiratory tract. The insensible water losses can be calculated using equations of the literature (e.g., Tokura et al., Int. J. Biometeor., 22(4):271-278 (1978); Mathias et al., J. Invest. Dermatol., 77:219-220 (1981); and Wilson et al., Br. J. Dermatol., 119:647-652 (1988)).

$$m_{persp-a} = (6.0 + 1.75*(P_{sp} - P_a)/7.5)*Bsa*t$$

with $P_{sp}$=skin water vapor pressure (mmHg)

In an embodiment, the data entered by the user to calculate insensible water losses ($m_{persp-a}$) comprises length of the activity (t), weight, height, and ambient temperature and/or humidity. Necessary data not entered by the user can be calculated from equations in the literature.

Figure 2:
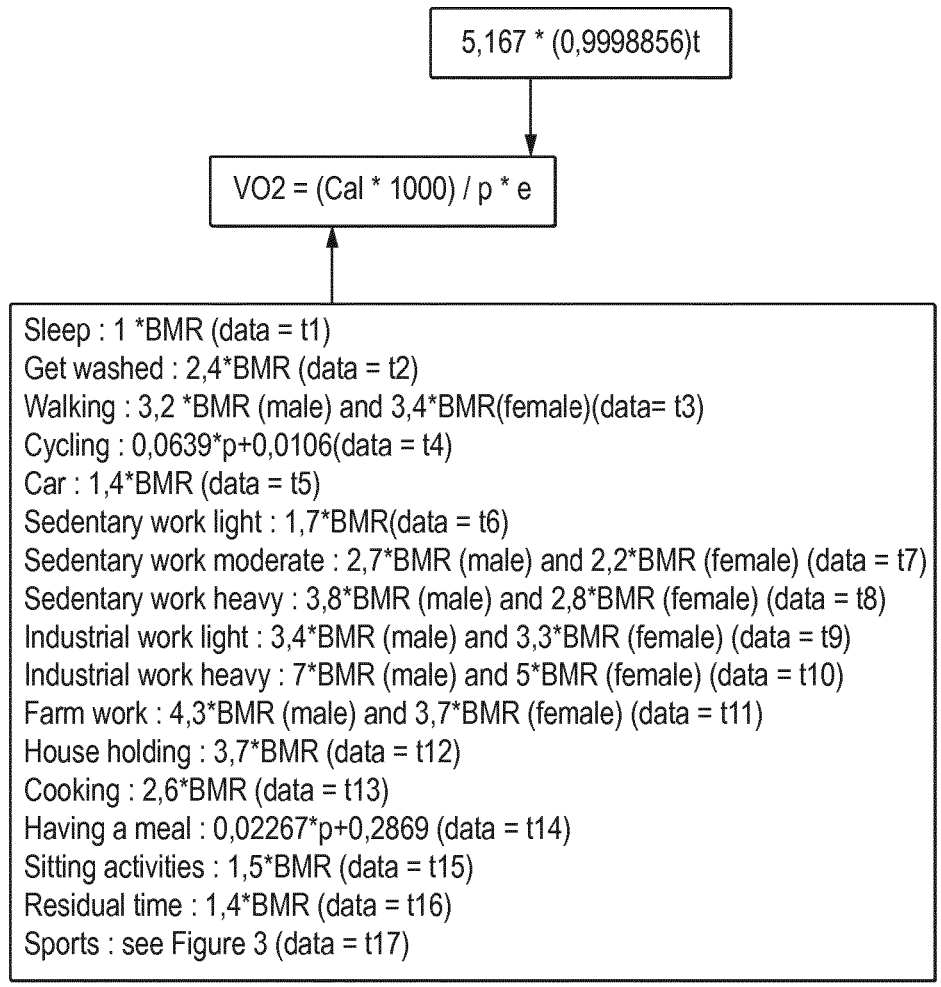
FIG. 2 shows user input identifying a plurality of activities and determination of the $VO_2$ of the individual from the plurality of activities in one or more embodiments of the methods provided by the present disclosure.

FIG. 2 generally illustrates an embodiment of calculations for estimating the $VO_2$ for each activity. The gender and age of the individual can be used to calculate the Basal Metabolic Rate (BMR) which in turn can be used to estimate the average caloric expenditure for each activity, and the can be used to calculate the $VO_2$ for each activity.

For example, a preferred embodiment of the application estimates the BMR as $(17.5*p+651)/1440$ if the individual is a male from 10-18 years old, estimates the BMR as $(15.3*p+679)/1440$ if the individual is a male from 19-30 years old, estimates the BMR as $(11.6*p+879)/1440$ if the individual is a male from 31-60 years old, estimates the BMR as $(13.5*p+487)/1440$ if the individual is a male who is at least 60 years old, estimates the BMR as $(12.2*p+746)/1440$ if the individual is a female from 10-18 years old, estimates the BMR as $(14.7*p+496)/1440$ if the individual is a female from 19-30 years old, estimates the BMR as $(8.7*p+829)/1440$ if the individual is a female from 31-60 years old, and estimates the BMR as $(10.5*p+596)/1440$ if the individual is a female who is at least 60 years old.

Then the BMR may be applied in a caloric expenditure equation specific for the corresponding activity. In this regard, non-limiting examples are shown in FIG. 2 for which the application has an equation for the caloric expenditure of sleeping, an equation for the caloric expenditure of washing oneself, an equation for the caloric expenditure of walking, an equation for the caloric expenditure of biking, an equation for the caloric expenditure of driving or riding in a car, an equation for the caloric expenditure of light sedentary work, an equation for the caloric expenditure of moderate sedentary work, an equation for the caloric expenditure of heavy sedentary work, an equation for the caloric expenditure of light industrial work, an equation for the caloric expenditure of heavy industrial work, an equation for the caloric expenditure of farm work, an equation for the caloric expenditure of housework, an equation for the caloric expenditure of cooking, an equation for the caloric expenditure of having a meal, an equation for the caloric expenditure of sitting, and an equation for the caloric expenditure of residual time.

Figure 3:
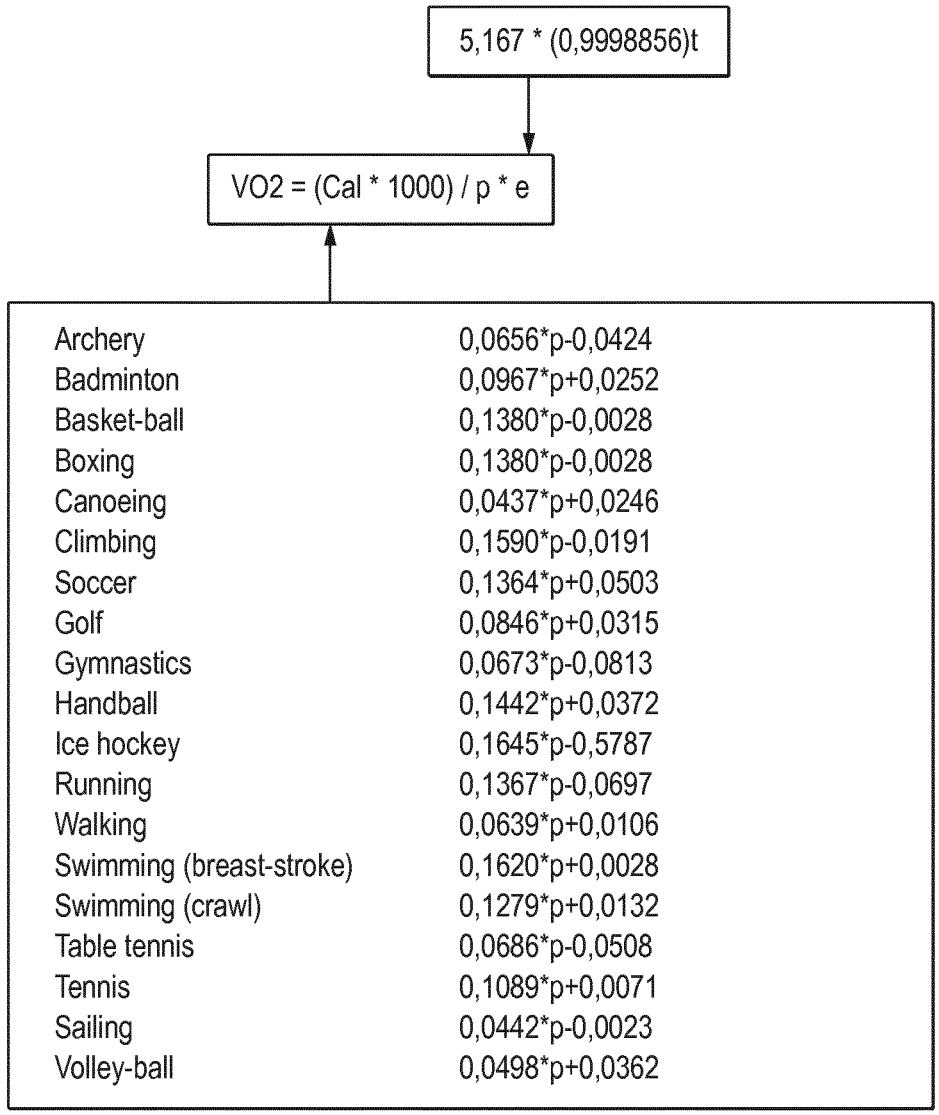
FIG. 3 shows determination of the volume of urine lost during a plurality of activities ($m_u$) in liters in one or more embodiments of the methods provided by the present disclosure.

FIG. 3 shows non-limiting examples of different caloric expenditure equations for different sports, such as an equation for the caloric expenditure of archery, an equation for the caloric expenditure of badminton, an equation for the caloric expenditure of basketball, an equation for the caloric expenditure of boxing, an equation for the caloric expenditure of canoeing, an equation for the caloric expenditure of climbing, an equation for the caloric expenditure of soccer, an equation for the caloric expenditure of golf, an equation for the caloric expenditure of gymnastics, an equation for the caloric expenditure of handball, an equation for the caloric expenditure of ice hockey, an equation for the caloric expenditure of running, an equation for the caloric expenditure of walking, an equation for the caloric expenditure of breast-stroke swimming, an equation for the caloric expenditure of crawl swimming, an equation for the caloric expenditure of table tennis, an equation for the caloric expenditure of breast-stroke sailing, and an equation for the caloric expenditure of volleyball.

Water losses can include urine loss from each activity ($m_{u-a}$), and urine loss can be deduced from several equations and data from literature involving glomerular filtration rate, renal plasma flow, hematocrit, cardiac output, and stroke volume (e.g., Poortmans J R, Sports Medicine, 1:125-153 (1984)). All these factors can be linked to heart rate at rest and $VO_2$ max, and heart rate at rest ($Fc_r$) and $VO_2$ max can be entered by the user or calculated by the program.

$$m_{u-a} = a*10^{-7}*Fc_r*(67+20.61*((VO_2 \max *p/1000) - 2.0))*t$$

with a=2.16 for male and a=2.36 for female, t=length of activity (min), $Fc_r$=heart rate at rest (bpm), p=weight (kg), $VO_2$ max=maximal consumption of oxygen (mL·min$^{-1}$·kg$^{-1}$)

In an embodiment, the data entered by the user to calculate urine loss from the activity ($m_{u-a}$) comprises length of activity (t), heart rate at rest ($Fc_r$), age and/or $VO_2$ max (if known). Necessary data not entered by the user can be calculated from equations in the literature. In an embodiment, if the heart rate at rest ($Fc_r$) is not known, the heart rate at rest ($Fc_r$) can be calculated using a heart rate at rest of 65 bpm.

Figure 4:
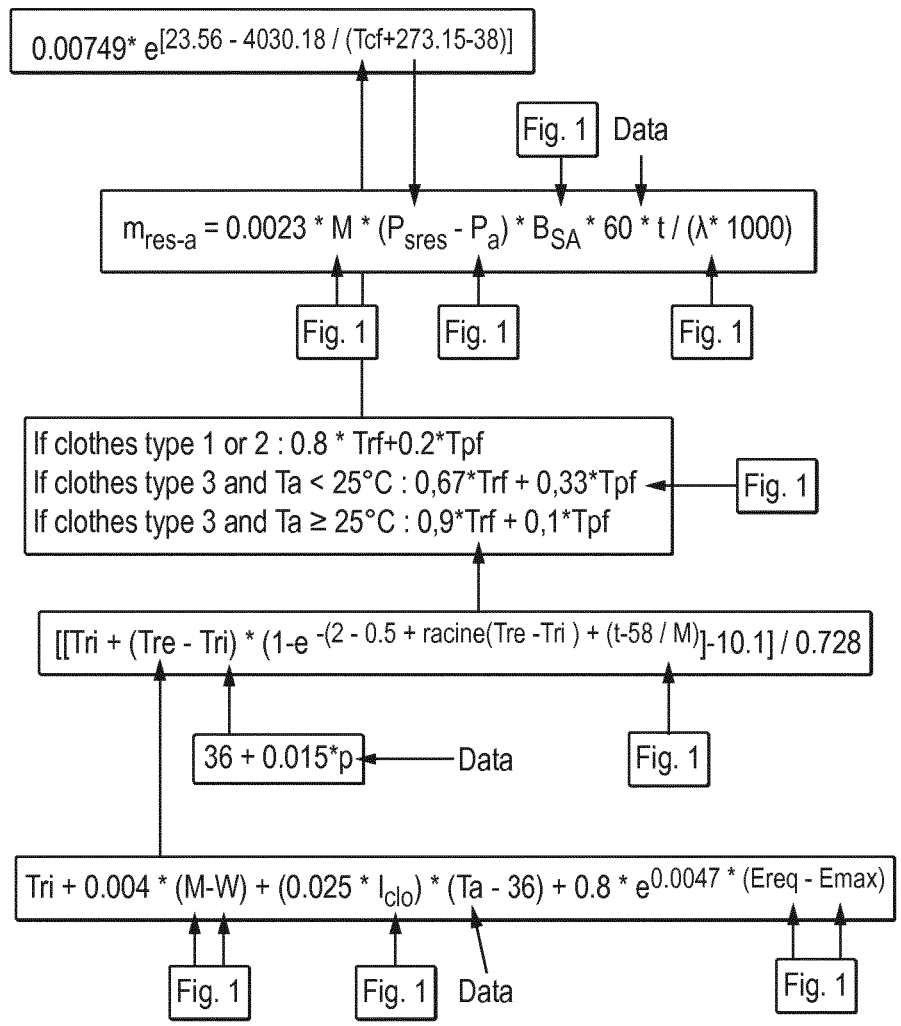
FIG. 4 shows determination of the volume of water lost by breathing during a plurality of activities ($m_{res}$) in liters in one or more embodiments of the methods provided by the present disclosure.

Water losses can include respiratory loss from each activity ($m_{res-a}$). FIG. 4 generally illustrates an embodiment of calculations for estimating the volume of respiratory loss during an activity ($m_{res-a}$) in liters.

Respiratory loss due to breathing has been deduced from several literature data (e.g., Kerslake D. McK. The stress of hot environments. Monographs of the Physiological Society no 29, Cambridge, University Press; and Ferrus L. et al. Respiration Physiology, 39:367-381 (1980)) and can be summarized as:

$$m_{res-a} = 0.0023*M*(P_{sres} - P_a)*Bsa*60*t/(\lambda*1000)$$

with M=metabolic heat (W·m$^2$), $P_{sres}$=saturated water vapor pressure of respiratory tract (mmHg), $P_a$=ambient water vapor pressure (mmHg), Bsa=Body surface (m$^2$), $\lambda$=vaporization latent heat (J·g$^{-1}$)

In an embodiment, the data entered by the user to calculate respiratory loss from the activity ($m_{res-a}$) comprises length of the activity (t), weight, height, age, gender, and ambient temperature. Necessary data not entered by the user can be calculated from equations in the literature.

Determination of respiratory water loss can include calculating the skin temperature ($T_p$) of the individual. The initial skin temperature ($T_{pi}$) (e.g., at rest or when the activity begins) and the final skin temperature ($T_{pf}$) (e.g., when the activity ends).

$T_{pi}$ is finally linked to dry ambient temperature ($T_a$) with the following equation:

$$T_{pi}=c*(36+0.015*p)$$

with c dependent of the clothes worn

In the same way, $T_{pf}$ has been calculated from raw data of scientific papers representing 221 subjects and is linked to $T_a$:

$T_{pf}=d*T_a+b$ with $d$ and $b$ depending of type of clothes (shorts+$T$-shirt versus long sleeve shirt/tracksuit or protection clothes)

The application can use the respiratory quotient (QR) as calculated in FIG. 1, along with the glucose ratio supplied by neoglucogenesis (Neo), to estimate the volume of water supplied by the body during an activity ($m_{met-a}$) in liters in one or more embodiments of the methods provided by the present disclosure.

The following calculations can be used to determine the glucose ratio supplied by neoglucogenesis (Neo) which can be used to determine the volume of water supplied by the body ($m_{met}$) during the activity.

If $t \leq 90$, $Neo=(0.0806*t+2.33)+16.99$

If $90 \leq t \leq 240$, $Neo=1.1643*(0.0806*t+2.33)+13.943$

If $t>240$, $Neo=40.5$

Then the metabolic water during the activity ($m_{met-a}$) can be calculated using the following equation.

$$m_{met-a}=(VO_2*p*t*e/10^6)*(0.0144+(0.1417*QR)-Neo*(0.00000031*t+0.00000904))/1000$$

As shown in FIG. 5, the application can request data from the individual regarding an amount of water intake from food products consumed during the plurality of activities ($m_{diet}$). In this regard, one or more of the plurality of activities can be categorized as a snack/meal. As a non-limiting example, the application can inquire how many different servings of specific food categories are consumed per day and then determine the water intake from food products consumed ($m_{diet}$) using the number of servings of each food category, the average water content of each food category and the average serving size of each food category.

The total of water needs per day in liters ($m_{eau}$) can then be determined as follows.

If $m_s \geq m_{persp}$, $m_{eau}=m_s+m_u+m_{res}-m_{met}-m_{diet}$

If $m_s < m_{persp}$, $m_{eau}=m_{persp}+m_u+m_{res}-m_{met}-m_{diet}$ where $m_s$=sum ($m_{s-a}$) for each activity (including any sport), $m_u$=sum ($m_{u-a}$) for each activity (including any sport), $m_{res}$=sum ($m_{res-a}$) for each activity (including any sport), $m_{persp}$=sum ($m_{persp-a}$) for each activity (including any sport), and $m_{met}$=sum ($m_{met-a}$) for each activity (including any sport)

In an embodiment, the application can determine the daily caloric balance in the individual, preferably by determining the daily caloric intake in kCal ($Cal_{int}$) and the daily caloric expenditure kCal ($Cal_{exp}$) and then determining the difference between these two values (Caloric balance=$Cal_{int}$-$Cal_{exp}$). The daily caloric expenditure kCal ($Cal_{exp}$) can be calculated by adding the caloric expenditures of each of the activities of the day. The daily caloric intake kCal ($Cal_{int}$) can be calculated using the data from the individual regarding an amount of water intake from food products consumed ($m_{diet}$). As a non-limiting example, the daily caloric intake kCal ($Cal_{int}$) can be calculated for the data in FIG. 5 as follows.

$$Cal_{int}=[89.80-(0.12*85)]*n1/100+[89.80-(0.12*60)]*(n2/100)+[89.80-(0.12*75)]*n3/100+[89.80-(0.12*65)]*n4/100+[89.80-(0.12*50)]*n5/100+[89.80-(0.12*84)]*n6/100+[89.80-(0.12*75)]*n7/100+[89.80-(0.12*35)]*n8/100$$

In an embodiment, the program determines mineral losses in the individual participating in a sport. The daily hydration plan can include information regarding maintaining a mineral level.

For example, sodium losses in grams ($m_{Na}$) can be calculated as follows:

If the individual practices a regular training,
$m_{Na}=Ar_{dc}\{0.66*m_s+1.035*m_u\}$ $Ar_{dc}$ is the number rounded to the upper decimal.

If the individual does not practice a regular training,
$m_{Na}=Ar_{dc}\{1.15*m_s+1.035*m_u\}$ Golf is automatically considered as "no regular training."

Calcium losses in mg ($m_{Ca}$) can be determined by $m_{Ca}=60*m_s$.

Magnesium losses in mg ($m_{Mg}$) can be determined by $m_{Mg}=24*m_s$.

Accordingly, an aspect of the present disclosure is a method of decreasing or preventing dehydration in an individual. Another aspect is a method of improving daily performance of an individual.

The methods can comprise accepting user input into an application provided by a device comprising a processor, the user input comprising information selected from the group consisting of a characteristic of the individual, a characteristic of each of a plurality of activities of which a day is comprised, and a combination thereof.

The characteristic of the individual can be selected from the group consisting of weight, height, gender, heart rate at rest, maximal heart rate, $VO_2$ max, effort intensity for the activity, a type of clothes worn during the activity, and combinations thereof. The characteristic of the activity is selected from the group consisting of the specific category of activity, a time duration, a location, an ambient temperature at the location, a humidity at the location, and combinations thereof. Preferably at least a portion of the user input (e.g., at least a portion of the information) is accepted before the activity, most preferably the entirety of the user input.

The device providing the application can analyze the information provided by the user input to determine a water loss by the individual in the plurality of activities. The analyzing of the information to determine the water loss can comprise determination of one or more (preferably all) of (i) water loss in sweat by the individual in each of the plurality of activities, (ii) water loss in urine by the individual in each of the plurality of activities, (iii) respiratory water loss by the individual in each of the plurality of activities, (iv) insensible water loss by the individual in each of the plurality of activities, (v) endogenic water formed by the individual in each of the plurality of activities, and (vi) water intake from food products consumed during the plurality of activities. In some embodiments, the usual amount of water intake is included in the determination such that the water loss by the individual in the each of the plurality of activities determined by the application is the usual water loss by the individual during the day.

Preferably at least a portion of the analyzing is completed before the plurality of activities, most preferably the entirety of the analyzing. In an embodiment, the analyzing is performed automatically by the device and/or the application in response to the user input providing the information.

The device providing the application can display a personalized daily hydration plan that comprises an amount of water intake for a day, based on analysis of the information provided by the user input. For example, the personalized hydration plan can be based at least partially on one or more of the water loss in sweat, the water loss in urine, the respiratory water loss, the insensible water loss, the endogenic water, and the water intake from food products consumed during the plurality of activities. In an embodiment, the creation and/or the display of the personalized hydration plan are performed automatically by the device and/or the application after the analyzing of at least a portion (preferably all) of the information.

In some embodiments, the method further comprises analyzing the information to determine a loss during the plurality of activities of at least one mineral selected from the group consisting of sodium, calcium and magnesium. In such embodiments, the daily hydration plan further comprises an intake amount of the at least one mineral for the individual.

Preferably, consumption of water by the individual according to the personalized daily hydration plan will result in the individual having a hydration level at the end of the day (or a time proximate to the end of the day, such as one hour after the end or thirty minutes after the end) that is at least approximately equal to the hydration level at the start of the plurality of activities (or a time proximate to the beginning, such as one hour before the start or thirty minutes before the start).

Yet another aspect of the present disclosure is a method in which a usual amount of water intake by the individual in a day is analyzed. The method can decrease or prevent dehydration in an individual participating in the activities of their day and/or improve daily performance of an individual participating in the daily activities.

The method can comprise accepting user input into an application provided by a device comprising a processor, the user input comprising a usual amount of daily water intake by the individual, information regarding the plurality of activities of which the day is comprised, and information regarding one or more characteristics of the individual.

The characteristic of the individual can be selected from the group consisting of weight, height, gender, heart rate at rest, maximal heart rate, $VO_2$ max, a type of clothes worn during one or more of the activities, and combinations thereof. The characteristic of the activity can be selected from the group consisting of a specific category of activity, a time duration, an effort level of the activity, a location, an ambient temperature at the location, a humidity at the location. Preferably at least a portion of the user input (e.g., at least a portion of the information) is accepted before the day for which the daily hydration plan is being obtained, most preferably the entirety of the user input.

The device providing the application can analyze the user input to determine a water loss by the individual in the plurality of activities of the day. The analyzing of the information to determine the water loss can comprise determination of one or more (preferably all) of (i) total water loss in sweat by the individual from the plurality of activities of the day, (ii) total water loss in urine by the individual from the plurality of activities of the day, (iii) total respiratory water loss by the individual from the plurality of activities of the day, (iv) insensible water loss by the individual from the plurality of activities of the day, and (v) total endogenic water formed by the individual during the plurality of activities of the day. In some embodiments, the usual amount of water intake is included in the determination such that the total water loss by the individual during the plurality of activities of the day as determined by the application is the usual daily water loss by the individual. In an embodiment, the analyzing is performed automatically by the device and/or the application in response to the user input providing the information.

The device providing the application can display an output on the device. When the total water loss from the usual daily amount of water intake by the individual from the plurality of activities of the day is less than a threshold, the output preferably is a first output that is a confirmation that the usual amount of daily water intake by the individual is sufficient to prevent dehydration for such a day. When the water loss from the usual daily amount of water intake by the individual is more than the threshold, the output preferably is a second output comprising a personalized daily hydration plan that comprises an amount of water intake based at least partially on the water loss determined from the information. In an embodiment, the display of the output is performed automatically by the device and/or the application after the analyzing of at least a portion (preferably all) of the information.

The personalized daily hydration plan (e.g., the total amount of daily water intake) can be based at least partially on one or more of the total water loss in sweat, the total water loss in urine, the total respiratory water loss, the total insensible water loss, the total daily endogenic water and the total daily amount of water intake from food products consumed during the plurality of activities.

Preferably, consumption of water by the individual according to the personalized daily hydration plan will result in the individual having a hydration level at the end of the day (or a time proximate to the end, such as one hour after the end or thirty minutes after the end) that is at least approximately equal to the hydration level at the start of the day (or a time proximate to the beginning, such as one hour before the start or thirty minutes before the start).

In some embodiments of the methods disclosed herein, the method further comprises administering water to the individual according to the personalized daily hydration plan.

In any of the embodiments disclosed herein, the program (e.g., an application) can be executed by a device of a user who is preferably the individual participating in the plurality of activities of the day or an individual involved in providing hydration to such an individual. The device can be a stationary and/or mobile communications device, for example at least one of a mobile telephone, such as a smartphone; a laptop computer; a desktop personal computer; a tablet; or a personal digital assistant. The program can be executed and/or stored by the device. The program can be obtained by the device using wired and/or wireless networks, for example the internet, telephone lines, WiFi/WLAN, 3G networks, or the like.

The device can store the program in a non-transitory computer readable storage medium that is any computer-readable media except for a transitory, propagating signal. Non-limiting examples of computer-readable media that can store the program include any type of disk including optical disks, CD-ROMs, and magnetic-optical disks; read-only memories (ROMs); random access memories (RAMs); EPROMs; EEPROMs; magnetic or optical cards; program specific integrated circuits (ASICs); and any type of media suitable for storing electronic instructions.

The program can be obtained and/or can be accessed by selection of a corresponding icon using the device. The icon can visually indicate the identity of the program, such as by depicting a representation of water, a beverage, or a beverage container. In an embodiment, the program can be obtained from an application store for the corresponding type of device or operating system of the device. In an embodiment, the program can be accessed using a web browser and the internet.

The device providing the application can provide a user interface that can accept information and display information. The user can enter the information into the data fields using any known input component of the device providing the application, such as a keyboard, a touchscreen, a trackball, and the like, and the present disclosure is not limited to a specific embodiment of the input component of the device.

The application can request that the user enter into the user interface information regarding the individual and their plurality of activities, for example one or more of the date of the plurality of activities, the time of each of the plurality of activities, the humidity of each of the plurality of activities, the location of each of the plurality of activities, the age of the individual, the weight of the individual, the duration of each of the plurality of activities, the heart rate at rest of the individual, the $VO_2$ max of the individual, and how much water the individual usually consumes during the each of the plurality of activities.

Then the application can analyze the information, for example using the calculations detailed above, and display the calculated water losses, e.g., one or more of $m_u$, $m_s$, $m_{res}$; the calculated water intake, e.g., one or more of $m_{met}$ and $m_{diet}$; and/or the total water need during the day $m_{eau}$ In a preferred embodiment, the application displays the water deficit of the individual at the end of the day using their usual hydration.

The application can confirm that the usual hydration is acceptable, for example if their estimated weight loss is about zero. Additionally or alternatively, the application can provide an optimal personalized hydration plan and can display the expected weight loss of the individual at the end of the each of the plurality of activities based on the daily hydration plan, which preferably is less than the weight loss using their usual hydration.

The application can display an optimal personalized hydration plan that identifies an amount of water to drink during the day.

In an embodiment, the application can identify mineral losses of the individual at the end of the day using their usual hydration, for example one or more of $m_{Ca}$, $m_{Mg}$, or $m_{Na}$. The hydration plan can include a suggestion to include a suggested amount of one or more of calcium, magnesium, or sodium; and the individual can ensure that these are included in the food products consumed during the day.

Data fields for the user to input the information can be displayed on one or more screens of the user interface, and the results of the analysis thereof can be displayed on one or more same screens and/or one or more different screens.

Other information and criteria not known to be related to dehydration at the time of this patent application but later discovered to be a factor can be used by the application, and the present disclosure is not limited to the above examples of the information and the criteria. The information and the criteria can be any information and criteria found to be related to loss of hydration, e.g., dehydration, in an individual participating in a plurality of activities during a day.

In some embodiments, the device providing the application preferably creates a profile for the user such that the profile is stored and can be edited using the user interface. The device providing the application can store at least a portion of the profile. Alternatively or additionally, a remotely located database can store at least a portion of the profile. In an embodiment, the remotely located database is connected to the device by a wireless network, such as the internet.

Accordingly, another aspect of the present disclosure is a device configured to perform at least part of one or more of the methods disclosed herein.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

Abbreviations

A Age (years old)
BSA Body surface ($m^2$)
C Heat exchange by convection ($W \cdot m^{-2}$)
Cal Average caloric expenditure for the effort ($kCal \cdot min^{-1}$)
$C_{res}$ Respiratory dry heat ($W \cdot m^{-2}$)
$D_c$ Cardiac output ($L \cdot min^{-1}$)
$E_{max}$ maximal evaporative capacity ($W \cdot mmHg^{-1} \cdot m^{-2}$)
$E_{req}$ required evaporative cooling ($W \cdot ° C.^{-1} \cdot m^{-2}$)
$E_{res}$ Respiratory heat loss ($W \cdot m^{-2}$)
e Oxygen energetic equivalent ($kcal \cdot L^{-1}$)
$F_{cf}$ Final heart rate (bpm)
$F_{ci}$ Initial heart rate (bpm)
$Gly_f$ Final glycemia ($g \cdot L^{-1}$)
h Height (m)
$H_a$ Ambient moisture (%)
$H_p$ Skin moisture (%)
Hep Glucose ratio supplied by liver glycogen (%)
I Activity intensity (%)
$I_{clo}$ Clothes thermal resistance coefficient ° C. $\cdot m^2 \cdot W^{-1}$
$I_m$ Clothes permeability index
M Metabolic heat ($W \cdot m^{-2}$)
$m_{Ca}$ Calcium losses (mg)
$m_{eau}$ Total water needs (L)
$m_g$ Fat mass (kg)
$m_{Glu}$ Glucose losses (g)
$m_m$ Lean mass (kg)
$m_{Na}$ Sodium losses (g)
$m_{Mg}$ Magnesium losses (mg)
$m_{met}$ Metabolic water (volume of water supplied by the body) (L)
$m_s$ Sweat losses (L)
$m_u$ Urine losses (L)
$m_{res}$ Respiratory losses (L)
Neo Glucose ratio supplied by neoglucogenesis (%)
p Weight (kg)
$P_a$ Ambient water vapor pressure (mmHg)
$P_{sa}$ Ambient saturated water vapor pressure (mmHg)
$P_p$ Weight loss (Pp1, Pp2) (%)
$P_{sp}$ Skin saturated water vapor pressure (mmHg)
$P_{sres}$ Respiratory tract saturated water vapor pressure (mmHg)
QR Respiratory quotient (no units)
R Heat exchange by radiation ($W \cdot m^{-2}$)
R+C Combined dry heat ($W \cdot m^{-2}$)
t Length of activity (min)
$T_a$ Dry ambient temperature (° C.)
$T_{ci}$ Initial body temperature (° C.)
$T_{cf}$ Final body temperature (° C.)
$T_{pf}$ Final skin temperature (° C.)

$T_{pi}$ Initial skin temperature (° C.)
$T_{re}$ Equilibrium rectal temperature (° C.)
$T_{rf}$ Final rectal temperature (° C.)
$T_{ri}$ Initial rectal temperature (° C.)
$VO_2$ max Maximal oxygen consumption (mL·min$^{-1}$·kg$^{-1}$)
$V_e$ Volume usually consumed during effort (L)
W Mechanical work done (W·m$^{-2}$)
w Index of skin humidification by sweat (no units)
λ Vapor latent heat (J·g$^{-1}$)
λ' Corrective factor to vapor latent heat (J·g$^{-1}$)
λf Final vapor latent heat (J·g$^{-1}$)
η Sweating efficacy (no units)

The invention is claimed is follows:

1. A dehydration prevention system comprising: at least one processor;
   a memory coupled to the at least one processor, wherein the memory stores instructions which, when executed by the at least one processor, cause the at least one processor to:
   receive a user input representing at least one activity of a plurality of user activities for a user and at least one characteristic of the user, wherein the user input identifies food products consumed during the plurality of user activities;
   analyze the user input to determine a total water loss by the user and determine a personalized hydration plan based on the at least one activity and the total water loss;
   cause a display device to display aspects of the personalized hydration plan, including a recommended total amount of water intake for a plurality of potential activities;
   determine a total amount of water intake from the food products and to determine the total water loss based at least in part on the total amount of water intake from the food products;
   determine an amount of endogenic water formed by the user during each of the plurality of activities and to determine the total water loss by the user from the plurality of activities based on at least partially on the endogenic water formed by the user in each of the plurality of activities;
   determine the total water loss in sweat by the user for each user activity represented by the user input;
   determine the total water loss by calculating water loss in urine by the user for each of the plurality of user activities and to determine the personalized hydration plan based at least partially on the determined water loss in urine by the user for each of the plurality of user activities;
   determine the total water loss by the user by determining a component water loss for each of the plurality of user activities and to determine the personalized hydration plan based at least partially on a respiratory water loss by the user for each of the plurality of user activities;
   determine the total water loss by the user by determining an insensible water loss by the user in each of the plurality of user activities and to determine the personalized hydration plan based at least partially on the determined insensible water loss; and
   calculate the total water loss by adding (i) the total water loss in sweat and/or the insensible water loss from the plurality of user activities, (ii) the water loss in urine from the plurality of user activities, and (iii) the respiratory water loss from the plurality of user activities, and subtracting (iv) the endogenic water from the plurality of user activities and (v) the total amount of water intake from the food products consumed during the plurality of user activities.

2. The dehydration prevention system of claim 1, wherein a total time duration of the plurality of user activities is approximately twenty-four hours, and the personalized hydration plan is a daily hydration plan.

3. The dehydration prevention system of claim 1 wherein the user input is associated with a first user activity, and the instructions, when executed by the at least one processor, further cause the at least one processor to analyze the first user activity using at least one variable or equation different from analysis of a different, second user activity even if the user input is otherwise identical.

4. The dehydration prevention system of claim 1 wherein the user input identifies a specific category of activity for each of the at least one activity, and the instructions, when executed by the at least one processor, further cause the at least one processor to (a) determine acaloric expenditure for each activity based on at least one selected from the group consisting of a time duration of the activity, an age of the user, a gender of the user, and a weight of the user and (b) determine the personalized hydration plan based at least partially on the determined caloric expenditure.

5. The dehydration prevention system of claim 1 wherein the at least one characteristic of the user is selected from the group consisting of weight, height, gender, heart rate at rest, maximal heart rate, maximal consumption of oxygen (VO2 max), a type of clothes worn during the plurality of user activities, and combinations thereof.

6. The dehydration prevention system of claim 1 wherein the instructions, when executed by the at least one processor, further cause the at least one processor to determine the personalized hydration plan prior to the user participating in the plurality of user activities.

7. The dehydration prevention system of claim 1 wherein the personalized hydration plan includes at least one suggestion for the user to improve daily performance during the plurality of user activities by achieving at least one of decreased fatigue, increased motivation, improved mood, or better cognitive functioning.

8. A method of decreasing or preventing dehydration from a plurality of activities of an individual, the method comprising:
   accepting user input into an application provided by a device comprising a processor, the user input comprising information identifying one or more characteristics of each of the plurality of activities and identifying one or more characteristics of the individual;
   analyzing the information provided by the user input to determine a total water loss by the individual from the plurality of activities, and the analyzing is performed by the device providing the application,
   the analyzing comprising:
   identifying food products consumed during the plurality of activities, determining a total amount of water intake from the food products, and determining the total water loss based at least in part on the total amount of water intake from the food products,
   determining an amount of endogenic water formed by the individual during each of the plurality of activities and determining the total water loss by the individual from the plurality of activities based on at least partially on the endogenic water formed by the individual in each of the plurality of activities,
   determining the total water loss in sweat by the individual for each activity represented by the user input, determining the total water loss by calculating water loss in urine by the individual for each of the plurality of activities and determining a personalized hydration plan based at least partially on the determined water loss in urine by the individual for each of the plurality of activities, determining the total water loss by the individual by determining a component water loss for each of the plurality of activities and determining the personalized hydration plan based at least partially on a respiratory water loss by the individual for each of the plurality of activities, determining the total water loss by the individual by determining an insensible water loss by the individual in each of the plurality of activities and determining the personalized hydration plan based at least partially on the determined insensible water loss, and calculating the total water loss by adding (i) the total water loss in sweat and/or the insensible water loss from the plurality of activities, (ii) the water loss in urine from the plurality of activities, and (iii) the respiratory water loss from the plurality of activities, and subtracting (iv) the endogenic water from the plurality of activities and (v) the total amount of water intake from the food products consumed during the plurality of activities; and displaying on the device the personalized hydration plan that comprises a recommended total amount of water intake for the plurality of activities, and the personalized hydration plan is based at least partially on the total water loss determined from the information.

9. The method of claim 8, wherein a total time duration of the plurality of activities is approximately twenty-four hours, and the personalized hydration plan is a daily hydration plan.

10. The method of claim 8, wherein the user input is associated with a first activity, and the analyzing comprises analyzing the first activity using at least one variable or equation different from analysis of a different, second activity even if the user input is otherwise identical.

11. The method of claim 8, wherein the analyzing further comprises (a) determining a caloric expenditure for each activity based on at least one selected from the group consisting of a time duration of the activity, an age of the individual, a gender of the individual, and a weight of the individual and (b) determining the personalized hydration plan based at least partially on the determined caloric expenditure.

12. The method of claim 8, wherein the one or more characteristic of the individual is selected from the group consisting of weight, height, gender, heart rate at rest, maximal heart rate, maximal consumption of oxygen (VO2 max), a type of clothes worn during the plurality of activities, and combinations thereof.

13. A device comprising a processor configured to accept user input into an application provided by the device, the user input comprising information identifying one or more characteristics of each of a plurality of activities of an individual and identifying one or more characteristics of the individual;

the processor further configured to analyze the user input to determine a total water loss by the individual from the plurality of activities by identifying food products consumed during the plurality of activities, determining a total amount of water intake from the food products, and determining the total water loss based at least in part on the total amount of water intake from the food products, determining an amount of endogenic water formed by the individual during each of the plurality of activities and determining the total water loss by the individual from the plurality of activities based on at least partially on the endogenic water formed by the individual in each of the plurality of activities, determining the total water loss in sweat by the individual for each activity represented by the user input, determining the total water loss by calculating water loss in urine by the individual for each of the plurality of activities and determining a personalized hydration plan based at least partially on the determined water loss in urine by the individual for each of the plurality of activities, determining the total water loss by the individual by determining a component water loss for each of the plurality of activities and determining the personalized hydration plan based at least partially on a respiratory water loss by the individual for each of the plurality of activities, determining the total water loss by the individual by determining an insensible water loss by the individual in each of the plurality of activities and determining the personalized hydration plan based at least partially on the determined insensible water loss, and calculating the total water loss by adding (i) the total water loss in sweat and/or the insensible water loss from the plurality of activities, (ii) the water loss in urine from the plurality of activities, and (iii) the respiratory water loss from the plurality of activities, and subtracting (iv) the endogenic water from the plurality of activities and (v) the total amount of water intake from the food products consumed during the plurality of activities;

the processor further configured to display on the device the personalized hydration plan comprising a recommended total amount of water intake for the plurality of activities of the individual, and the personalized hydration plan is based at least partially on the total water loss by the individual from the plurality of activities.

* * * * *